United States Patent
Clarion et al.

(10) Patent No.: US 10,597,414 B2
(45) Date of Patent: Mar. 24, 2020

(54) CRYSTALLINE POLYMORPHIC FORM OF 3-HYDROXY-4,5-BIS-BENZYLOXY-6-BENZYLOXYMETHYL-2-PHENYL-2-OXO-2λ5-[1,2]OXAPHOSPHINANE

(71) Applicant: PHOST'IN, Montpellier (FR)

(72) Inventors: Ludovic Clarion, Compbailleux (FR); Séverine Loiseau, Vailhauques (FR); Pierric Marchand, Rouen (FR); Morgan Pauchet, Mont Saint Aignan (FR)

(73) Assignee: PHOST'IN, Montpellier (FR)

( * ) Notice: Subject to any disclaimer, the term of this patent is extended or adjusted under 35 U.S.C. 154(b) by 0 days.

(21) Appl. No.: 16/332,983

(22) PCT Filed: Sep. 19, 2017

(86) PCT No.: PCT/EP2017/073682
§ 371 (c)(1),
(2) Date: Mar. 13, 2019

(87) PCT Pub. No.: WO2018/054925
PCT Pub. Date: Mar. 29, 2018

(65) Prior Publication Data
US 2019/0330252 A1    Oct. 31, 2019

(30) Foreign Application Priority Data
Sep. 20, 2016  (EP) .................................. 16306202

(51) Int. Cl.
*C07F 9/6571*   (2006.01)
*A61P 35/00*    (2006.01)

(52) U.S. Cl.
CPC ........ *C07F 9/657172* (2013.01); *A61P 35/00* (2018.01); *C07B 2200/13* (2013.01)

(58) Field of Classification Search
CPC ...................... C07F 9/657172; C07B 2200/13
See application file for complete search history.

(56) References Cited

FOREIGN PATENT DOCUMENTS

WO    2009/004096 A1    1/2009

OTHER PUBLICATIONS

The International Search Report (ISR) with Written Opinion for PCT/EP2017/073682 dated Nov. 3, 2017, pp. 1-10.
Clarion, Ludovic et al. Oxaphosphinanes: New Therapeutic Perspectives for Glioblastoma Journal of Medicinal Chemistry (2012) vol. 55, pp. 2196-2211.

*Primary Examiner* — Noble E Jarrell
(74) *Attorney, Agent, or Firm* — McDonnell Boehnen Hulbert & Berghoff LLP

(57) ABSTRACT

The present invention relates to a novel crystalline polymorphic form of 3-Hydroxy-4,5-bis-benzyloxy-6-benzyloxymethyl-2-phenyl-2-oxo-2λ5-[1,2]oxaphosphinane and a method for preparing the same.

16 Claims, 7 Drawing Sheets

CRYSTALLINE POLYMORPHIC FORM OF 3-HYDROXY-4,5-BIS-BENZYLOXY-6-BENZYLOXYMETHYL-2-PHENYL-2-OXO-2λ5-[1,2]OXAPHOSPHINANE

CROSS-REFERENCE TO RELATED APPLICATIONS

This application is a U.S. national phase of International Application No. PCT/EP2017/073682, filed Sep. 19, 2017, which claims priority from European Patent Application no. 16306202.9, filed Sep. 20, 2016, the disclosure of each of which is hereby incorporated by reference in its entirety.

TECHNICAL FIELD

The present invention relates to a novel crystalline polymorphic form of 3-Hydroxy-4,5-bis-benzyloxy-6-benzyloxymethyl-2-phenyl-2-oxo-2λ5-[1,2]oxaphosphinane and a method for preparing the same.

BACKGROUND ART

3-Hydroxy-4,5-bis-benzyloxy-6-benzyloxymethyl-2-phenyl-2-oxo-2λ5-[1,2]oxaphosphinane (additional name: 4,5-bis(benzyloxy)-6-((benzyloxy)methyl)-3-hydroxy-2-phenyl-1,2-oxaphosphinane 2-oxide) is referred to as "Compound I" in the present invention. Compound I is a compound (also called 3.48 or 3.1 in previous documents) that has been proven to be an efficient anti-cancer agent and in particular for reducing or preventing the appearance of metastases, as described by the PCT applications WO2009/004096 and WO2014/128429, respectively. Compound I and its use against glioblastoma is more specifically disclosed in J. Med. Chem. 2012, 55, 2196-2211. The example of method provided in this document to synthesise compound I allows its formation in a four diastereoisomers mixture, arising from the creation of two chiral centers. From the four formed enantiopure diastereoisomers, the most potent diastereoisomer is PST3.1a.

As disclosed in the cited prior art, synthesis of PST3.1a (also referred herein as compound of formula (I)) can be performed by reacting 2,3,5-tri-O-benzylarabinose 3 and ethyl phenylphosphinate 4 as shown in Scheme 1 below.

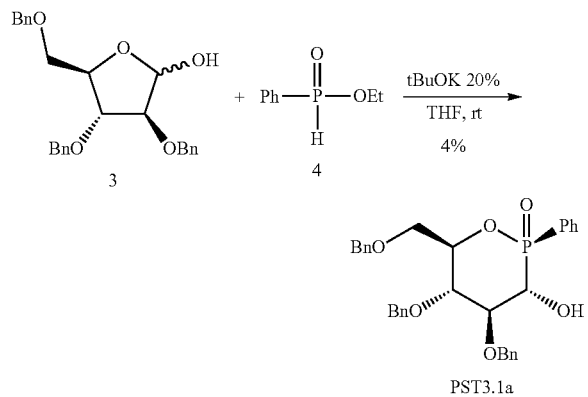

Treatment of an equimolar of 3 and 4 in THF (Tetrahydrofuran) followed by addition of potassium tert-butoxide actually provides a mixture of 4 diastereoisomers in about equimolar amount. The 4 diastereoisomers mixture is called in the present description "mixture A" and the diastereoisomers comprised therein are represented below (Scheme 2).

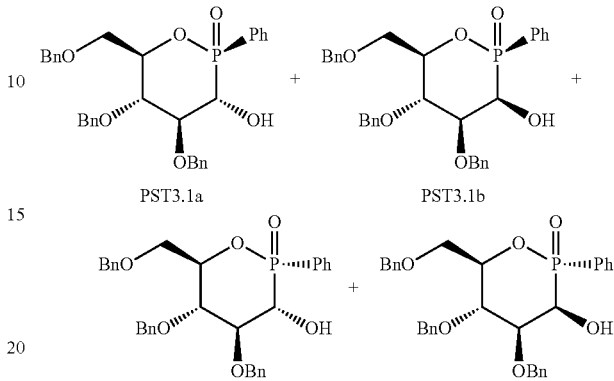

After stirring of the obtained mixture (mixture A) and evaporation of the solvent, chloroform was added and the obtained organic solution was washed with ammonium chloride, dried, filtered, and the solvent evaporated to obtain a yellow oil residue containing the four diastereoisomers. After purification on silica gel chromatography, separation of the four diastereoisomers by chromatography on preparative reverse-phase HPLC can be performed. However, the global yield of PST3.1a is low (about 4%). Other chromatography or fractional crystallization-based methods have been performed in an attempt to increase the overall yield of PST3.1a. However, technical specifications, solvents and/or purification techniques involved in these methods do not allow it to be efficiently and easily converted into an industrial scale.

A permanent aim in organic synthesis is to create synthesis processes that can be transposed into industrial conditions. In order to meet requirements for industrial processes, different parameters of the synthesis are to be optimized. First, solvents must be as little volatile as possible, in order to be easily recoverable. Thus, chlorinated volatile solvents, e.g. dichloromethane, chloroform and/or carbon tetrachloride, are preferably avoided. In addition, the numbers of equivalents of reagents required are preferably limited, the temperatures involved preferably remain in an easily accessible range, and easy to proceed purification steps should be privileged. Finally, reaction mixtures and isolated product are preferably thermally stable.

Current Good Manufacturing Practice (c-GMP) has been defined for preparation of drug products for administration to humans or animals. GMP regulations require a quality approach to manufacturing, enabling companies to minimize or eliminate instances of contamination, mixups, and errors. GMP regulations address issues including recordkeeping, personnel qualifications, sanitation, cleanliness, equipment verification, process validation, and complaint handling.

To the Applicant knowledge, no industrially applicable process to synthesise compound PST3.1a has been described so far.

Hence, an object of the present invention is to provide a process for preparing PST3.1a that can be adapted easily and efficiently to industrial scale, as compared to the process of the prior-art wherein unsafe compounds, such as chloroform and diethyl ether, and/or column chromatography are used.

Moreover, since a highly pure form, typically greater than 99.0 percent, of any drug is generally required for human treatment, a method that combines the control of the formation of isomers and a readily final purification is particularly advantageous.

Furthermore, in addition to the method issues, it is the aim of the invention to provide solid state physical properties of Compound I. These properties can be influenced by controlling the conditions under which Compound I is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must necessitate the use of glidants such as colloidal silicon dioxide, talc, starch, or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulation syrups, elixirs, and other liquid medicaments. The solid state form of a compound can also affect its behavior on compaction and its storage stability.

These practical physical characteristics are influenced by the conformation and orientation of molecules in the unit cell, which define a particular polymorphic form of a substance. The polymorphic form can give rise to a thermal behavior different from that of the amorphous material or another polymorphic form. Thermal behavior is measured in the laboratory by such techniques as capillary melting point, thermogravimetric analysis ("TGA"), and differential scanning calorimetry ("DSC") and can be used to distinguish some polymorphic forms from others. A particular polymorphic form can also give rise to distinct spectroscopic properties that can be detectable by powder x-ray crystallography and infrared spectrometry.

Generally, the crystalline solid has improved chemical and physical stability over the amorphous form, and forms with low crystallinity. It can also exhibit lower hygroscopicity, improved bulk properties, and/or flowability.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristics. There is a need in the art for crystalline Compound I and advantageous polymorphic forms thereof.

SUMMARY OF INVENTION

The present invention relates to a novel crystalline polymorphic form of 3-Hydroxy-4,5-bis-benzyloxy-6-benzyloxymethyl-2-phenyl-2-oxo-2λ5[1,2]oxaphosphinane which has high usability as a medicament, for use as a drug in human or veterinary medicine.

The present invention also concerns a method for the preparation of said crystalline polymorphic form, in particular starting from PST3.1a.

It also deals with the overall method for the preparation of said crystalline polymorphic form, more particularly starting from the reaction of 2,3,5-tri-O-benzylarabinose 3 with ethyl phenylphosphinate 4.

In another aspect, the present invention provides a pharmaceutical composition comprising the crystalline polymorphic form described herein, and more particularly made by the process of the present invention, and one or more pharmaceutically acceptable excipients.

The present invention further provides a process for preparing a pharmaceutical formulation comprising combining the crystalline polymorphic form described herein with at least one pharmaceutically acceptable excipient.

The present invention further provides the crystalline polymorphic form described herein as a medicament, in particular for use in the treatment of cancers and/or for a use for reducing or preventing the appearance of metastases in a patient afflicted with a cancer.

The present invention further provides for a use of the crystalline polymorphic form described herein for the manufacture of a pharmaceutical composition for the treatment of cancers and/or for reducing or preventing the appearance of metastases in a patient afflicted with a cancer.

BRIEF DESCRIPTION OF THE FIGURES AND ABBREVIATIONS

Unless otherwise stated, the following abbreviations and denominations are used throughout the description and claims of the present invention:

Ph=phenyl; Et=ethyl; tBu=tert-butyl; Ac=acetyl
THF=tetrahydrofuran
MeTHF=2-methyltetrahydrofuran
MTBE=methyltert-butylether
rt=room temperature
vol.=volume
eq.=equivalent
NMR=Nuclear Magnetic Resonance
HPLC=High Performance Liquid Chromatography FIG. 1 illustrates a powder X-ray diffraction pattern for the crystalline form of the invention characterized by x-ray powder diffraction reflections at about 8.65, 16.06, 16.53, 19.16 and 21.05±0.20 degrees two-theta (as prepared by example 1).

DETAILED DESCRIPTION OF THE INVENTION

Figure 1:
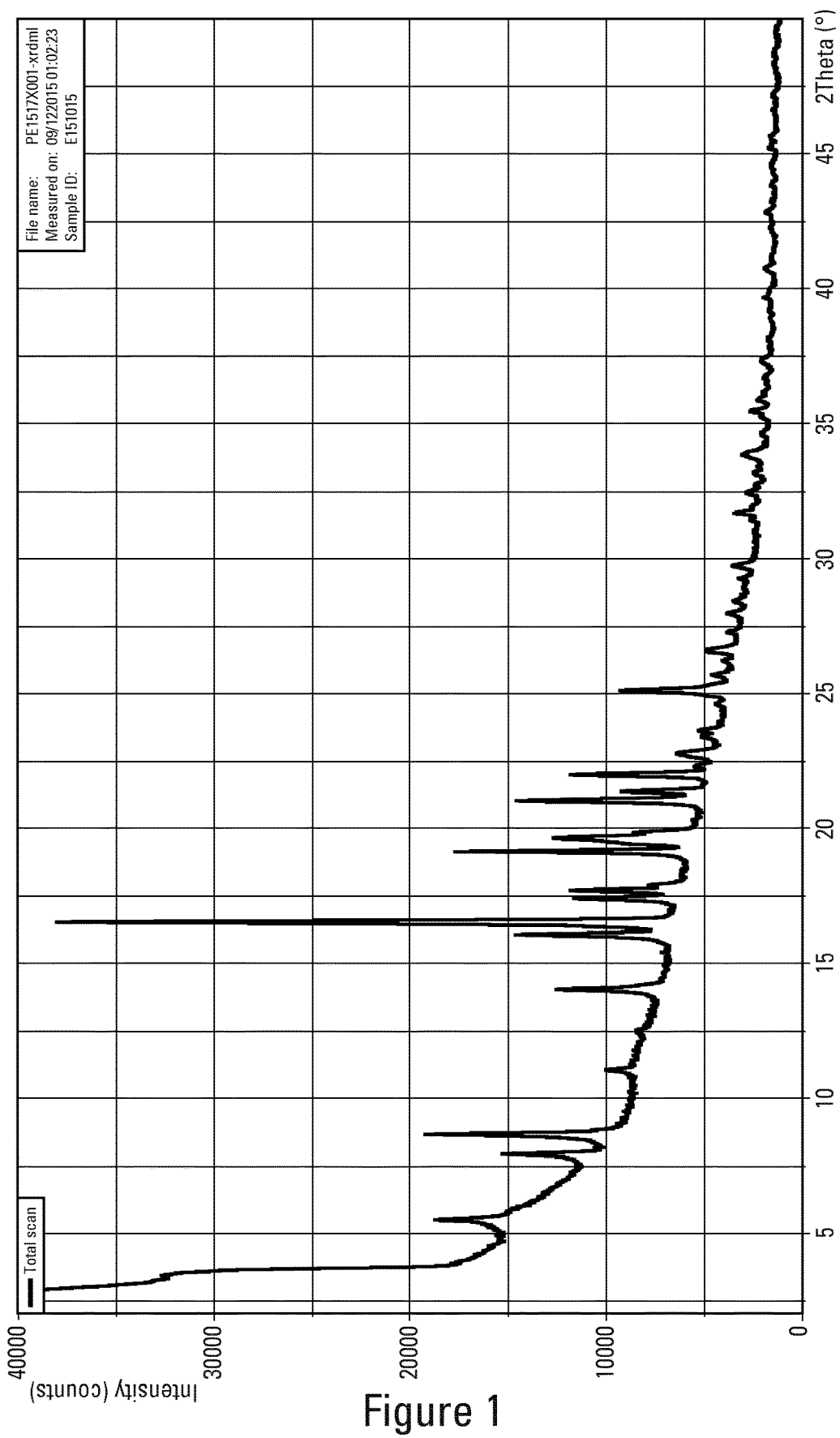

As used herein, the term "ambient temperature" or "room temperature" refers to a temperature of between about 15° C. to about 30° C.

In the present disclosure, the singular forms "a", "an" and "the" include the plural reference, and reference to a particular numerical value includes at least that particular value, unless the context clearly indicates otherwise. Thus, for example, a reference to "a solvent" is a reference to one or more of such solvents and equivalents thereof to those skilled in the art, and so forth.

As used herein, the term "about" or "around" will be understood by a person of ordinary skill in the art and will vary to some extent on the context in which it is used. If there are uses of the term which are not clear to persons of ordinary skill in the art given the context in which it is used, "about" or "around" will mean up to plus or minus 10% of the particular term.

The percentages are herein expressed by weight, unless otherwise specified.

According to the invention, the term "comprise(s)" or "comprising" (and other comparable terms, e.g., "containing," and "including") is "open-ended" and can be generally interpreted such that all of the specifically mentioned features and any optional, additional and unspecified features are included. It can also be interpreted as the phrase "consisting essentially of" where the specified features and any optional, additional and unspecified features that do not materially affect the basic and novel characteristic(s) of the claimed invention are included or the phrase "consisting of" where only the specified features are included, unless otherwise stated.

As used herein, the terms "treatment" or "therapy" (as well as different word forms thereof) includes preventative (e.g., prophylactic), curative, or palliative treatment. Such preventative, curative, or palliative treatment may be full or partial. For example, complete elimination of unwanted symptoms, or partial elimination of one or more unwanted symptoms would represent "treatment" as contemplated herein.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of the crystalline polymorphic form of the present invention will vary from patient to patient not only with the particular compound, component or composition selected, the route of administration, and the ability of the crystalline polymorphic form to elicit a desired response in the individual, but also with factors such as the disease state or severity of the condition to be alleviated, age, sex, weight of the individual, the state of being of the patient, and the severity of the condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the crystalline polymorphic form are outweighed by the therapeutically beneficial effects. As an example, the crystalline polymorphic form useful in the therapeutic methods of the present invention is administered at a dosage and for a time such that the rate of metastases and/or the appearance thereof are reduced as compared to the level thereof before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Each particular/preferred/specific embodiment specified herein may be combined with each other, unless incompatible.

The document J. Med. Chem. 2012, 55, 2196-2211, PCT applications WO2009/004096 and WO2014/128429 disclose isolation and recovery of PST3.1a by chromatography methods. However, the obtained solid forms were mixtures of polymorphic forms.

The present invention provides a crystalline form of compound I, characterized by powder x-ray diffraction reflections at about 8.65, 16.06, 16.53, 19.16 and 21.05±0.2, preferably ±0.1, degrees two-theta. This crystalline form can be further characterized by powder x-ray diffraction reflections at about 14.04, 17.69, 19.66, 22.02 and 25.12±0.2 degrees two-theta, or substantially as depicted in FIG. 1 or Table 1 below.

TABLE 1

| 2θ ° | $D_{spacing}$ Å | Intensity counts | Intensity % | 2θ ° | $D_{spacing}$ Å | Intensity counts | I % % |
|---|---|---|---|---|---|---|---|
| 2.35 | 37.56 | 585 | 2 | 24.62 | 3.61 | 481 | 2 |
| 5.50 | 16.05 | 4319 | 14 | 25.12 | 3.54 | 5446 | 17 |
| 7.92 | 11.16 | 4759 | 15 | 25.70 | 3.46 | 974 | 3 |
| 8.65 | 10.21 | 9662 | 31 | 26.25 | 3.39 | 561 | 2 |
| 11.07 | 7.99 | 1455 | 5 | 26.59 | 3.35 | 1515 | 5 |
| 12.54 | 7.05 | 594 | 2 | 27.27 | 3.27 | 603 | 2 |
| 14.04 | 6.30 | 5352 | 17 | 27.98 | 3.19 | 798 | 3 |
| 16.06 | 5.51 | 7852 | 25 | 28.45 | 3.13 | 630 | 2 |
| 16.53 | 5.36 | 31404 | 100 | 29.29 | 3.05 | 557 | 2 |
| 17.40 | 5.09 | 5099 | 16 | 29.74 | 3.00 | 1040 | 3 |
| 17.69 | 5.01 | 5410 | 17 | 31.47 | 2.84 | 328 | 1 |
| 17.90 | 4.95 | 1486 | 5 | 31.71 | 2.82 | 1157 | 4 |
| 19.16 | 4.63 | 11914 | 38 | 31.95 | 2.80 | 336 | 1 |
| 19.66 | 4.51 | 7009 | 22 | 32.50 | 2.75 | 623 | 2 |
| 19.84 | 4.47 | 2982 | 9 | 33.18 | 2.70 | 401 | 1 |
| 21.05 | 4.22 | 9412 | 30 | 33.86 | 2.64 | 1061 | 3 |
| 21.36 | 4.16 | 4149 | 13 | 35.31 | 2.54 | 343 | 1 |
| 22.02 | 4.03 | 6997 | 22 | 35.47 | 2.53 | 866 | 3 |
| 22.31 | 3.98 | 782 | 2 | 35.91 | 2.50 | 498 | 2 |
| 22.78 | 3.90 | 1851 | 6 | 37.36 | 2.41 | 472 | 2 |
| 23.44 | 3.79 | 882 | 3 | 42.87 | 2.11 | 418 | 1 |
| 23.65 | 3.76 | 1083 | 3 | 45.26 | 2.00 | 318 | 1 |

Preferably, this crystalline form of compound I of the invention has less than about 20% of any other form of compound I present, more preferably has less than about 10% of any other form of compound I present, even more preferably is in a substantially pure form, i.e. has less than about 5% of any other compound I form present, and most preferably has less than about 2% of any other compound I form present.

In a particular embodiment, the crystalline form of compound I of the invention has a melting point, by Differential Scanning calorimetry (DSC), of 175.5-177.5° C., more specifically 176.2° C.±0.4° C. (or ±0.3° C.), at a heating rate of 10° C./min.

In a particular embodiment, this crystalline form of compound I shows no significant weight loss, measured by thermal gravimetric analysis ("TGA") at the range of about 25° C. to 250° C., i.e. before and after its melting point. In a particular embodiment, water content of up to about 0.3% (w/w) was measured by Karl Fisher.

In a particular embodiment, the crystalline form of the invention is non-hygroscopic. More specifically, the Dynamic vapor sorption (DVS) analysis on the crystalline form of the invention shows weight loss lower than 0.1% on the relative humidity range studied (0% RH to 95% RH).

According to a particular embodiment, the volume equivalent sphere diameters measured by laser diffraction methods vary as follow: D10: from 70-80 nm, and/or D50%: from 140-160 nm, and/or D90: 360-380 nm. D10 D50, and D90 represent respectively the mean diameter of 10%, 50%, and 90% of the number of particles measured by laser diffraction methods. For example, the D10 diameter is the diameter at which 10% of the particles is comprised of smaller particles, and the D50 is the diameter at which 50% of particles is comprised of smaller particles.

Another object of the present invention relates to a method for the preparation of the crystalline form of the invention, comprising at least one crystallizing step of a solution comprising the isomer PST3.1a and acetone. Preferably, the solution is a saturated PST3.1a solution in acetone. In a more specific embodiment, the solution further comprises the isomer PST3.1b. The weight ratio of PST3.1a/PST3.1b in said solution may vary from 40/60 to 90/10, preferably from 50/50 to 90/10, and more specifically from 60/40 to 85/15.

The crystallising step (recrystallizing and separating) may include a cooling method (a method which comprises cooling a crystallization system), a poor-solvent addition method (a method which comprises adding a poor solvent to a crystallization system), and any other method. In a particular embodiment, the crystallisation step includes a cooling method. For the cooling method, the cooling rate is not particularly limited to a specific one. The cooling may be rapid cooling or preferably slow cooling. The cooling rate may be for example about 0.1 to 20° C./minute, preferably about 5 to 15° C./minute, and more preferably about 10 to 15° C./minute.

According to a preferred embodiment, the method for the preparation of the crystalline form of the invention comprises one, two, three, four, or five crystallizing steps. The crystallizing step of the solution comprising the isomer PST3.1a and acetone is preferably the last crystallization step. According to specific embodiments, the crystallizing step(s) preceding the crystallization step with acetone are carried out with a solution comprising the isomer PST3.1a and a solvent selected in the group consisting of acetone and ethanol, optionally in combination with water or methyl tert-butylether (MTBE). Preferably, the solution(s) of the crystallizing step(s) in the method of the invention are saturated PST3.1a solutions in the selected solvent.

According to a particular embodiment, the crystallizing step(s) preceding the crystallizing step with acetone is(are) carried out with solutions comprising the isomer PST3.1a and ethanol (optionally with water or MTBE, or preferably as the sole solvent-pure solvent). Preferably, two crystallizing steps with solutions comprising the isomer PST3.1a and ethanol are carried out, followed by one crystallizing step of the solution comprising the isomer PST3.1a and acetone.

The PST3.1a used in the crystallization step(s) can come from any known methods for preparing the same, such as the methods described in the cited prior art. Generally, PST3.1a is present in the mixture A (with the 3 other diastereoisomers as described previously) or in a mixture comprising PST3.1a and PST3.1b compounds, as the only diastereoisomers. The ratios of the diastereoisomers in the said mixtures may vary in a wide range and generally depends on the method for preparing the same. According to a preferred embodiment, before the crystallizing steps of the invention, the ratio of PST3.1a with respect to the other diastereoisomers in the mixture is the highest, but still unsatisfactory (such as less than 90%, or even less than 95 or 98%, measured by $^{31}P$ NMR). As specified above, in a specific embodiment, the mixture further comprises the isomer PST3.1b. The weight ratio of PST3.1a/PST3.1b in said mixture may vary from 40/60 to 90/10, preferably from 50/50 to 90/10, and more specifically from 60/40 to 85/15.

The crystallization step(s) described above allow not only to prepare a polymorphic form according to the invention and as described above, but allow also to increase the ratio of PST3.1a (with respect to the three other diastereoisomers, and in particular PST3.1b) up to 99% (measured by $^{31}P$ NMR) while giving rise to a satisfactory yield.

According to a particular embodiment, the PST3.1a implemented for the crystallization step(s) is prepared by the method comprising the following steps:

a. contacting 2,3,5-tri-O-benzylarabinose 3 and ethyl phenylphosphinate 4 in an organic solvent, in the presence of potassium tert-butoxide;
b. adding to the solution of step a) a neutralizing agent of potassium tert-butoxide;
c. adding a water-immiscible organic solvent to the mixture of step b) to allow decantation of the organic layer;
d. washing with water, followed by adding an ether-type or toluene solvent; and
e. recovery of PST3.1a, preferably by filtration.

The organic solvent of step a) can be of any type, more preferably it is selected in the group consisting of THF, methyl tert-butylether, ethyl acetate, MeTHF, acetone, toluene and a mixture thereof. In a particular embodiment, the solvent of step a) is THF.

The neutralizing agent of step b) can be any agent able to quench potassium tert-butoxide in step a). The neutralizing agent can be any highly diluted acid solution, including excess of water. In a particular embodiment, said neutralizing agent is NH4Cl.

The water-immiscible organic solvent of step c) can be dichloromethane, chloroform, or preferably ethyl acetate.

The solvent of step d) can be toluene or an ether-type such as isopropyl ether or, preferably, methyl tert-butylether.

According to a preferred embodiment, one molar equivalent is used for each compound 3 and 4 at step (a).

According to a preferred embodiment, step (a) is carried out at temperature from room temperature to 40° C., more preferably at room temperature, and preferably at about atmospheric pressure.

According to another embodiment, the method for the preparation of the crystalline polymorphic form of the invention comprises steps (a) to (e) as detailed above, followed by the recrystallization step(s) as described above.

In another aspect, the present invention provides a pharmaceutical composition comprising the crystalline polymorphic form described herein, and more particularly made by the method of the present invention, and one or more pharmaceutically acceptable excipients.

The present invention further provides a process for preparing a pharmaceutical formulation comprising combining the crystalline polymorphic form described herein with at least one pharmaceutically acceptable excipient.

The present invention further provides the crystalline polymorphic form described herein as a medicament, in particular for use in the treatment of cancers and/or for a use for reducing or preventing the appearance of metastases in a patient afflicted with a cancer.

The present invention further provides for a use of the crystalline polymorphic form described herein for the manufacture of a pharmaceutical composition for the treatment of cancers and/or for reducing or preventing the appearance of metastases in a patient afflicted with a cancer.

The present invention further provides for a method for the treatment of cancers and/or for reducing or preventing the appearance of metastases in a patient afflicted with a cancer by administering in a patient in need of such treatment an effective amount of the crystalline polymorphic form described herein.

In particular, the crystalline polymorphic form described herein is useful as an active principle in pharmaceutical compositions for human or veterinary use, intended for treating cancers (metastatic or primary), i.e. cancer cells, or for preventing the appearance of cancers, especially for reducing or preventing the appearance of metastases in a patient afflicted by a cancer. In the case where the patient is afflicted by a metastatic cancer, the crystalline polymorphic form described herein is especially directed in particular toward reducing or preventing the appearance of additional metastases.

In the present description, a patient denotes both an animal, in particular a non-human mammal, and a person. The term "patient afflicted by a cancer" means both a patient afflicted by a declared cancer (primary or metastatic) and a hidden cancer, i.e. invisible, the existence of which has been revealed, for example, by the discovery of metastases.

In the present description, cancer cells denote cells having typical characteristics of cells that cause cancer, such as uncontrolled proliferation, immortality, metastatic potential, rapid growth and high speed of proliferation, and certain specific morphological characteristics. Cancer cells are often in the form of a tumor, but such cells may exist alone in the body, or may be non-tumor-forming cancer cells, such as leukemic cells. Cancer cells may be associated with numerous types of cancers, comprising, without limitation, leukemia, a lymphoma, a melanoma, a neuroblastoma, liver cancer, ovarian cancer, brain cancer, lung cancer, bowel cancer, breast cancer, pancreatic cancer, prostate cancer, testicular cancer, esophageal cancer, uterine cancer, cervical cancer, kidney cancer, stomach cancer, bladder cancer, a cerebrospinal cancer or a colorectal cancer. The crystalline polymorphic form or the pharmaceutical compositions of the invention may be used for the therapeutic treatment of at least one of the cancers mentioned above.

When the crystalline polymorphic form according to the invention is used in the context of an antimetastatic treatment, the patient is afflicted with a "primary" cancer. This cancer is a cancer that is capable of metastatizing, which may be, without limitation, a melanoma, a glioblastoma multiform, a lung cancer, especially non-small-cell lung cancer, bowel cancer or colorectal cancer, breast cancer, prostate cancer, testicular cancer, cervical cancer, kidney cancer, preferably a glioblastoma multiform, breast cancer or non-small-cell lung cancer. The crystalline polymorphic form of the invention is particularly suited for treating the risk of metastasis in a patient afflicted with a glioblastoma multiform. It is now recognized that glioblastoma multiform (GBM), commonly known as glioblastoma, may be a cancer with metastatic potential giving rise to a generalized pathology (Schönsteiner, S. S. et al., Journal of Clinical Oncology 2011, 29, 23, 668-671). Cancer cells originating from glioblastomas may effectively cross the blood-brain barrier and establish extraneural metastases. The reported sites of extraneural metastases are the lungs, the pleura, the liver, cervical lymphatic nodules, bones and bone marrow.

The cancer is more particularly selected from glioblastoma multiform, breast cancer and non-small-cell lung cancer, preferably glioblastoma multiform.

A pharmaceutical composition comprising an anticancer compound of the invention presents equally in either a solid or a liquid form. In a liquid form, the pharmaceutical composition preferably comes as an aqueous suspension or as a non-aqueous suspension, or as a water-in-oil or an oil-in-water emulsion.

Amongst the pharmaceutical compositions of the invention, those compositions can be particularly mentioned, that are suitable for the oral, topical, parenteral, nasal, intravenous, percutaneous, transcutaneous, rectal, perlingual or airway administration, and especially simple or sugar coated tablets, sublingual tablets, capsules, lozenges, suppositories, creams, ointments, dermic gels, and oral intake or injection ampoules.

The dosage regimen varies depending on the sex, the age and the weight of the patient, depending on the administration route, and on the cancer type, the evolution state of the cancer, in particular on whether metastases have been detected in the patient or not. The dosage regimen may also vary depending on the type of associated anticancer treatment(s).

Generally speaking, a polymorphic form of the invention is used in amounts preferably ranging from 0.001 mg/kg of patient or animal body weight, to 1 g/kg of patient or animal body weight per 24 hours, in one or several drug intakes. Preferably, said amount is at least equal to 0.01 mg/kg, more preferably 0.05 mg/kg. Preferably, said amount is at most equal to 500 mg/kg, more preferably to 100 mg/kg.

To be administered by the oral route, a pharmaceutical composition according to the invention may present in the form of tablets, capsules, coated tablets, syrups, suspensions, solutions, powders, pellets, emulsions, suspensions of microspheres or nanospheres, lipid vesicle suspensions or various polymer-based vesicles.

To be administered by the oral route, a pharmaceutical composition according to the invention may be in the form of tablets that may be obtained from solid compositions comprising the crystalline polymorphic form of the invention in combination with various excipients such as microcrystalline cellulose, sodium citrate, calcium carbonate, dicalcium phosphate or glycine. Various disintegrating agents such as starch (corn, potato or tapioca starch, etc.), alginic acid or a silicate may be used. Binders such as polyvinyl pyrrolidone, sucrose, gelatin, or acacia may also be used. Lubricants such as magnesium stearate, sodium laurylsulfate, or even talc may also be used. Such solid compositions, as a powder, may be used for preparing gelatin capsules. For solid compositions, lactose or polyethylene glycol with a high molecular weight may also be used.

In order to prepare liquid compositions for oral administration, the crystalline polymorphic form may be combined with various sweeteners, flavouring agents, colouring agents, possibly together with emulsifying agents or suspending agents, in combination with diluents such as water, ethanol, propylene glycol, glycerin or any combination of these excipients.

To be administered by the parenteral route, a pharmaceutical composition according to the invention may present in the form of infusion or injection solutions and suspensions.

To be administered by the parenteral route, oil or water solutions or suspensions, emulsions, or implants may be used, in particular, including suppositories. For example, the crystalline polymorphic form may be dispersed in a liquid vehicle such as a liquid saline solution or a saline solution containing 5% by weight of dextrose, that are traditionally used for preparing pharmaceutical formulations for injection.

To be administered by the enteral route, controlled release compositions may be used, for example compositions wherein the crystalline polymorphic form is protected from the external environment by a plurality of coating layers that decompose in a different way, for example upon contact with a neutral or basic medium (enteric coatings) or upon contact with an aqueous medium (coating layers comprising soluble polymers or polymers that decompose in water).

Generally speaking, a pharmaceutical composition according to the invention comprises from 0.01% to 99% by weight, and advantageously from 1% to 90% by weight, of an anticancer compound, as compared to the total weight of the composition.

Generally speaking, a pharmaceutical composition according to the invention comprises from 1% to 99.99% by weight, and advantageously from 10% to 99% by weight of an excipient or a mixture of pharmaceutically acceptable excipients.

The pharmaceutical composition of the present invention may be used for a parenteral, topical or local administration, and in a prophylactic and/or therapeutic way. Thus, the anticancer compound according to the invention is prepared in a form that is adapted to the selected administration route, for example in a liquid or a freeze-dried form. The pharmaceutical compositions comprising the crystalline polymorphic form of the invention may contain an excipient and/or a liquid or solid, pharmaceutically acceptable vehicle, for example an aqueous vehicle. Many pharmaceutically acceptable excipients and/or vehicles may be used, for example, water, where appropriate in admixture with propylene glycol or polyethylene glycol, buffered water, a saline solution, a glycine solution and their derivatives as well as agents that are required to produce the physiologic conditions, as for example buffering agents and pH regulating agents, surfactants such as sodium acetate, sodium lactate, sodium chloride, potassium chloride, calcium chloride, this list being non limitative. In addition, the pharmaceutical composition may be sterilized using sterilization methods that are well known to those skilled in the art.

Suitable inert, non-toxic, pharmaceutically acceptable vehicles, adjuvants or excipients include as non-limitative examples, diluents, solvents/solubilizing agents, preservatives, wetting agents, emulsifying agents, dispersing agents, binders, swelling agents, disintegrating agents, capsulating agents, retardants, lubricants, absorbents, suspending agents, colouring agents, flavours, stabilizers, thickeners, etc. Such compounds are for example magnesium carbonate, magnesium stearate, talc, lactose, pectin, dextrin, starch, gelatin, cellulose-based materials, cacao butter, etc.

When preparing a solid composition in the form of tablets, the main active ingredient is mixed with a pharmaceutical vehicle such as gelatin, starch, lactose, magnesium stearate, talc, gum arabic or equivalents.

Tablets may be coated with sucrose or any other suitable starting material or they otherwise can be treated in such a way that they have a long-acting or a delayed activity and they release in a sustained manner a predetermined amount of active ingredient.

A capsule preparation is obtained by mixing the active ingredient with a diluent and by pouring the thus obtained mixture in soft or hard capsules.

A pharmaceutical composition in the form of a syrup or elixir may contain the active ingredient together with a sweetener, preferably a hypocaloric sweetener, methylparaben and propylparaben as antiseptic agents, as well as a flavouring agent and a suitable colouring agent.

Water dispersible powders or granules may contain the active ingredient in admixture with dispersing agents or wetting agents or suspending agents, such as polyvinyl pyrrolidone, as well as sweeteners or taste modifiers.

The crystalline polymorphic form, as active ingredient, may also be formulated in microcapsules, optionally with one or more supports or additives.

Generally speaking, for providing a pharmaceutical composition according to the present invention, those skilled in the art can advantageously refer to the most recent edition of the European Pharmacopoeia, for example to the 5th European Pharmacopoeia edition published in January 2005, or to the 6th European Pharmacopoeia edition, made publicly available in June 2007.

Methods for preparing pharmaceutical compositions according to the invention may be easily found by those skilled in the art, for example in Remington's Pharmaceutical Sciences, Mid. Publishing Co, Easton, Pa., USA.

Physiologically acceptable adjuvants, vehicles and excipients are also described in "Handbook of Pharmaceutical Excipients," Second Ed., American Pharmaceutical Association, 1994.

For formulating a pharmaceutical composition according to the invention, the man skilled in the art may advantageously refer to the most recent edition of the European Pharmacopoeia or the United States Pharmacopoeia (USP).

Those skilled in the art may especially advantageously refer to the USP 30-NF 25 edition of the United States Pharmacopoeia (USP).

When the pharmaceutical composition according to the invention comprises at least one pharmaceutically or physiologically acceptable excipient, it is in particular an excipient that is suitable for an oral administration of the composition or an excipient suitable for a parenteral administration of the composition.

The invention may be applied in combination with other therapeutic modalities, such as chemotherapy, cryotherapy, hyperthermia, radiotherapy, etc.

The present invention will now be illustrated with following non limitative examples.

EXAMPLES

Example 1

Synthesis of Compound I from Compound 3 and Compound 4

The synthesis of PST3.1a was performed starting from commercially available 2,3,5-tri-O-benzylarabinofuranose 3 and ethyl phenylphosphinate 4 (Scheme 1).

Scheme 1: synthesis of PST3.1a

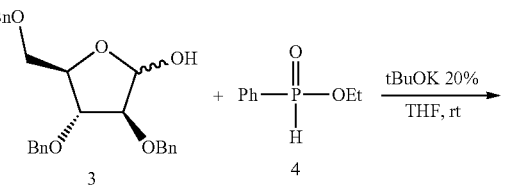

-continued

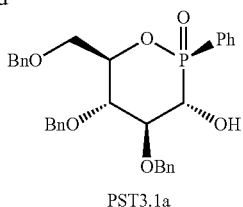

PST3.1a

Treatment of an equimolar mixture of 3 and 4 in THF by potassium tert-butoxide (tBuOK) provided a mixture of 4 diastereoisomers (scheme 2).

Scheme 2

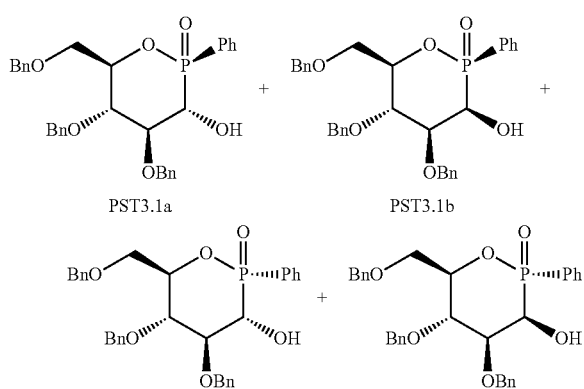

PST3.1a      PST3.1b

PST3.1b was the main impurity (the ratio PST3.1a/PST3.1b/other diastereoisomers obtained was: 29/31/39 (by $^{31}$P NMR).

The overall process (before crystallization step(s)) was the following (scheme 3):

Scheme 3

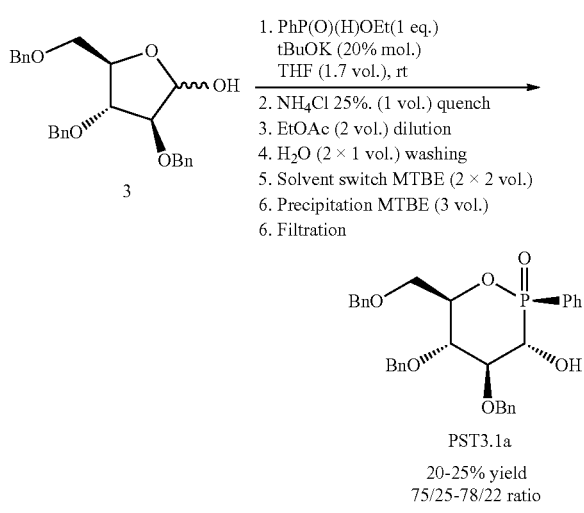

1. PhP(O)(H)OEt(1 eq.)
   tBuOK (20% mol.)
   THF (1.7 vol.), rt
2. NH$_4$Cl 25%. (1 vol.) quench
3. EtOAc (2 vol.) dilution
4. H$_2$O (2 × 1 vol.) washing
5. Solvent switch MTBE (2 × 2 vol.)
6. Precipitation MTBE (3 vol.)
6. Filtration PST3.1a
20-25% yield
75/25-78/22 ratio Ethyl acetate was thus added to the quenched mixture to allow decantation of the organic layer. After aqueous washings and without drying, solvents were switched to methyl tert-butylether (MTBE) under vacuum until precipitation occurred. MTBE was added and the resulting yellow suspension was filtered to afford crude PST3.1a in 20-25% yield (% by weight) and 75/25 to 78/22 PST3.1a/PST3.1b ratio (measured by $^{31}$P NMR). Both other diastereoisomers were removed from the mixture by MTBE.

The solvent switch was tested with isopropyl ether instead of MTBE: PST3.1a was isolated in good yield but in poor PST3.1a/PST3.1b ratio (45/55).

Crystallization Step(s)

Different solvents were tested in the crystallization process of a crude PST3.1a with a PST3.1a/PST3.1b ratio of 62/38 to improve yield and/or the 1a/1b ratio. The results are shown in Table 2.

TABLE 2

| Entry | Solvent | Volumes | Yield of recrystallization | Ratio 1a/1b (by $^{31}$P NMR) |
|---|---|---|---|---|
| 1 | Acetone | 11 | 45% | 88/12 |
| 2 | MTBE | 30 (partially insoluble) | 69% | 78/22 |
| 3 | Ethanol | 10 | 53% | 90/10 |
| 4 | Toluene | 10 | 53% | 74/26 |
| 5 | Isopropanol | 10 | 62% | 77/23 |
| 6 | Ethanol/water 1/1 | 36 | 59% | 83/17 |
| 7 | Ethanol/MTBE 1/2 | 23 | 42% | 84/16 |

The use of acetone on a crude mixture (62/38) (Table 2, entry 1) afforded PST3.1a in 45% yield in a 88/12 1a/1b ratio (similar to additional results: 45% yield, 87/13 1a/1b ratio from 64/36 1a/1b ratio crude compound). The recrystallization in MTBE (Table 2, entry 2) gave a good yield, but the increase of the ratio 1a/1b was limited even if the mixture of compounds was not fully soluble in 30 volumes of solvent. Ethanol showed very interesting results with a 90/10 ratio (Table 2, entry 3). Toluene and isopropanol (Table 2, entries 4 and 5) gave poor results. Availing of good results with ethanol, mixtures using this solvent were tested (Table 2, entries 6 and 7), interesting results were obtained but without improving the result in pure ethanol.

After this first screening of solvent, a full sequence of recrystallization was considered The sequence using acetone provided pure PST3.1a (99/1 ratio) in 10% yield after 3 recrystallizations.

After 3 recrystallizations in ethanol, only a 96/4 ratio was obtained but in 35% yield. Finally, an additional recrystallization in acetone provided pure PST3.1a (99/1 ratio) in 25% overall yield (recrystallization sequence).

Starting from a ratio of about 98/2, highly pure PST3.1a was obtained after 3 new recrystallizations in acetone (Scheme 4).

Scheme 4

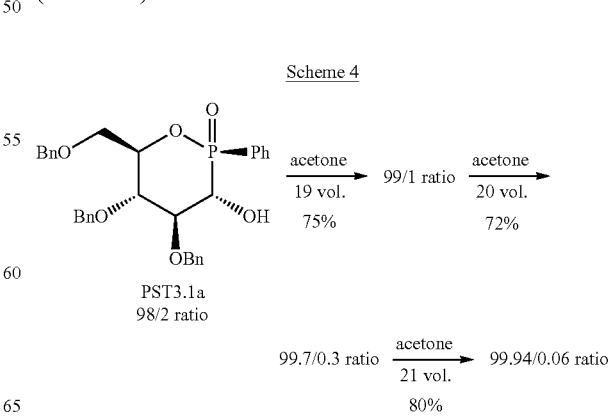

PST3.1a
98/2 ratio acetone
19 vol.
75%
→ 99/1 ratio acetone
20 vol.
72%
→

99.7/0.3 ratio
acetone
21 vol.
80%
→ 99.94/0.06 ratio

Finally, an overall method was implemented as shown in scheme 5. The synthesis of PST3.1a was performed on 263 grams of compound 3 to afford 26.7 g of final compound in 7.8% yield with a good PST3.1a/PST3.1b ratio.

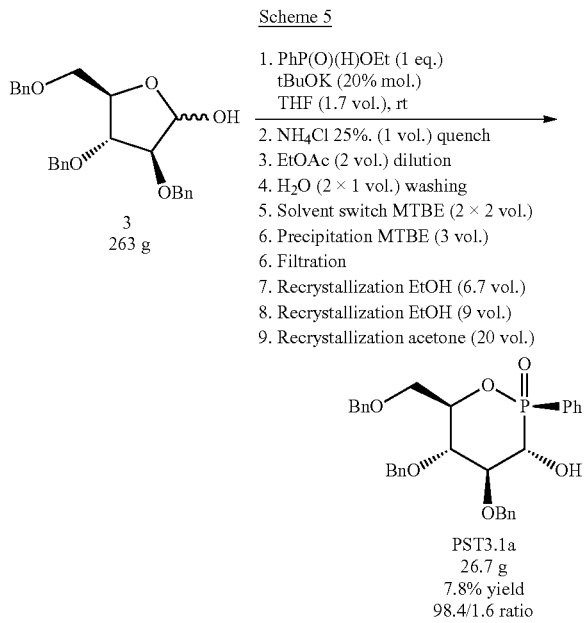

Scheme 5

Figure 6:
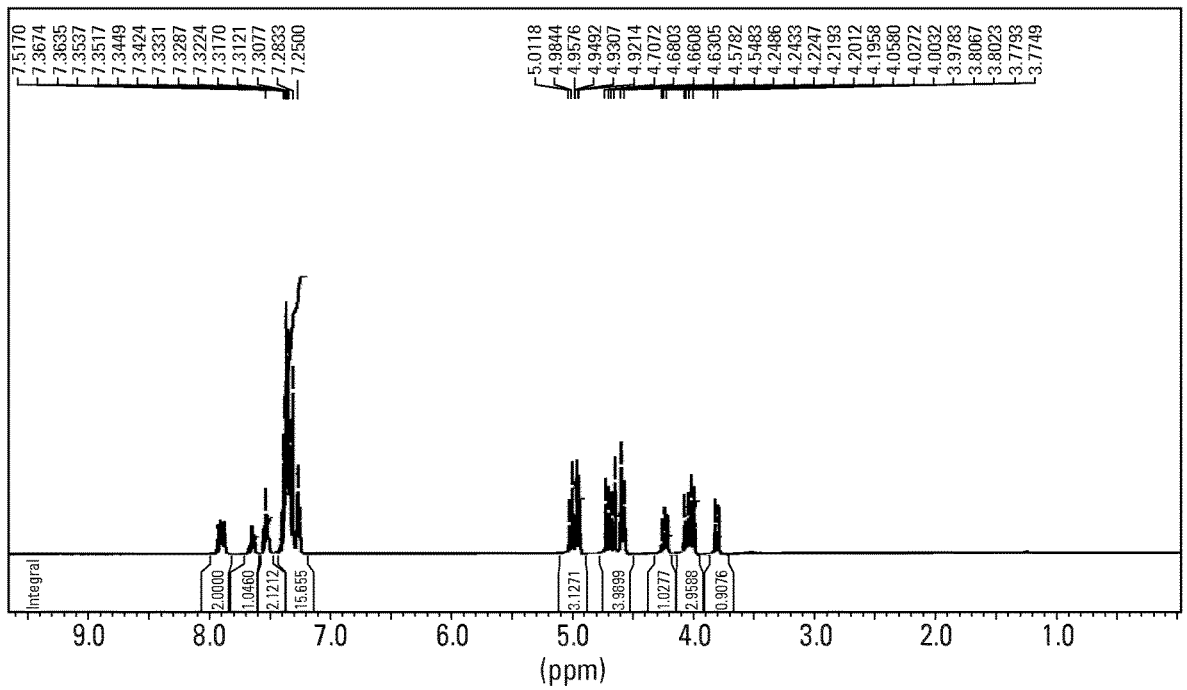
FIG. 6 is the RMN $^1$H-CDCl3 spectrum for the crystalline form of the invention (as prepared by example 1), including enlargement of ranges of interest (above)
Figure 6:
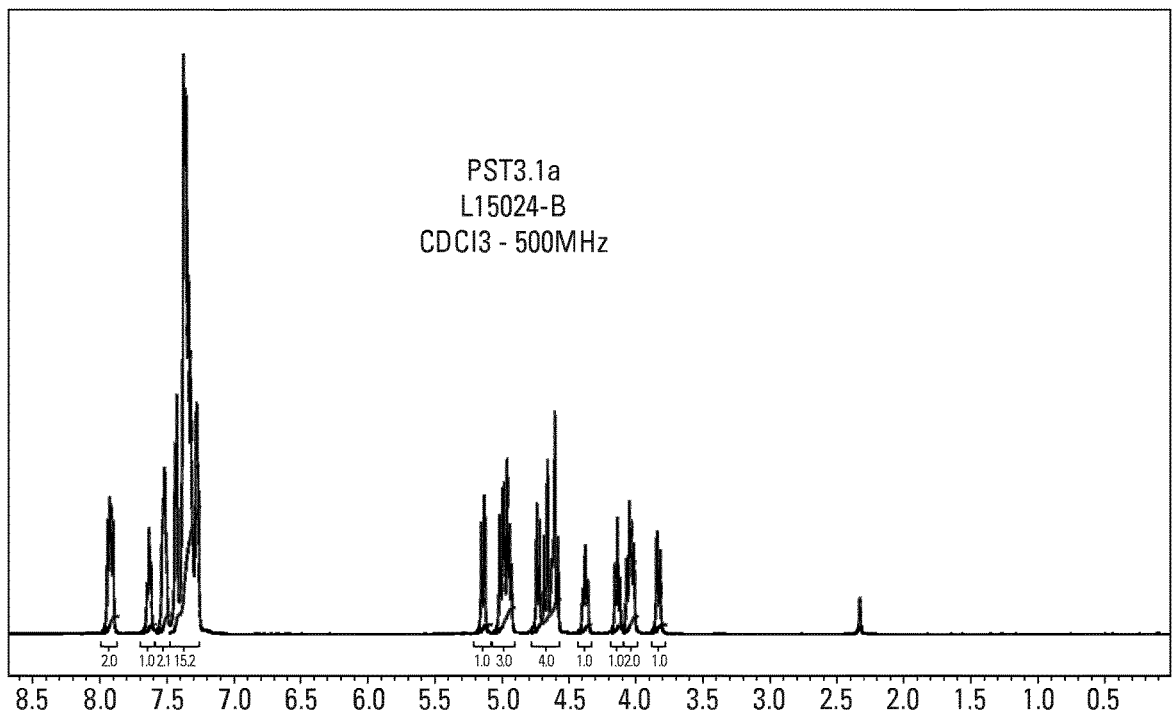
Figure 7:
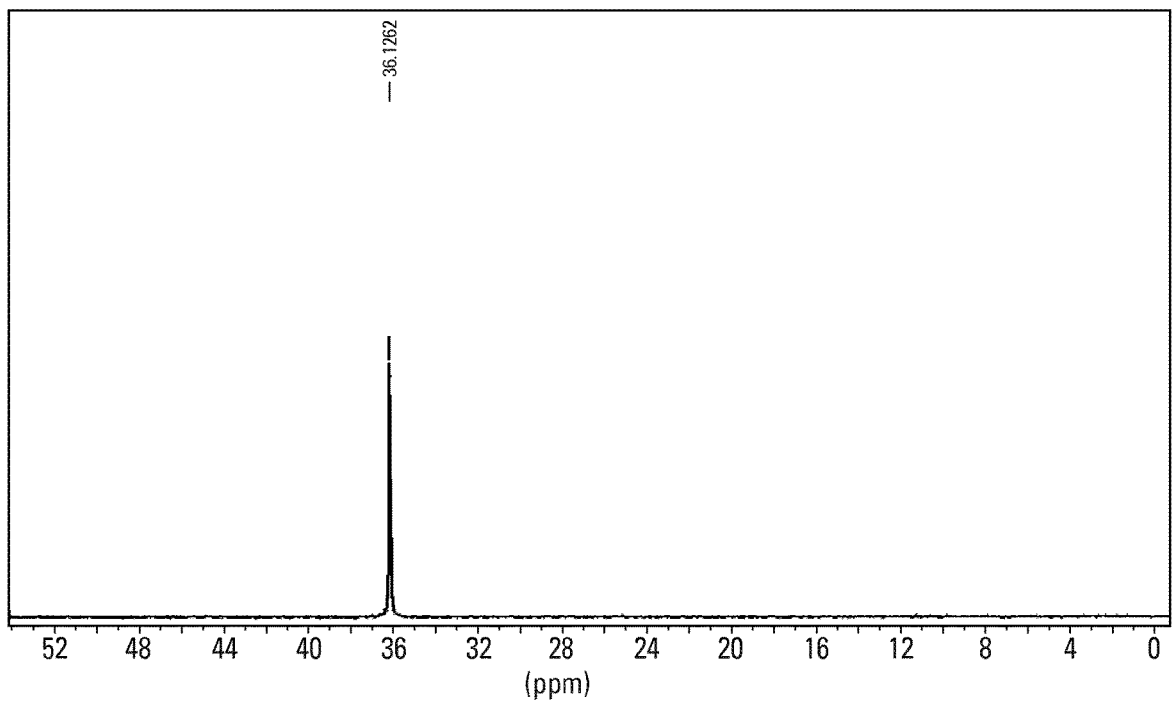
FIG. 7 is the RMN $^{31}$P spectrum for the crystalline form of the invention (as prepared by example 1), including enlargement of ranges of interest (above)
Figure 7:
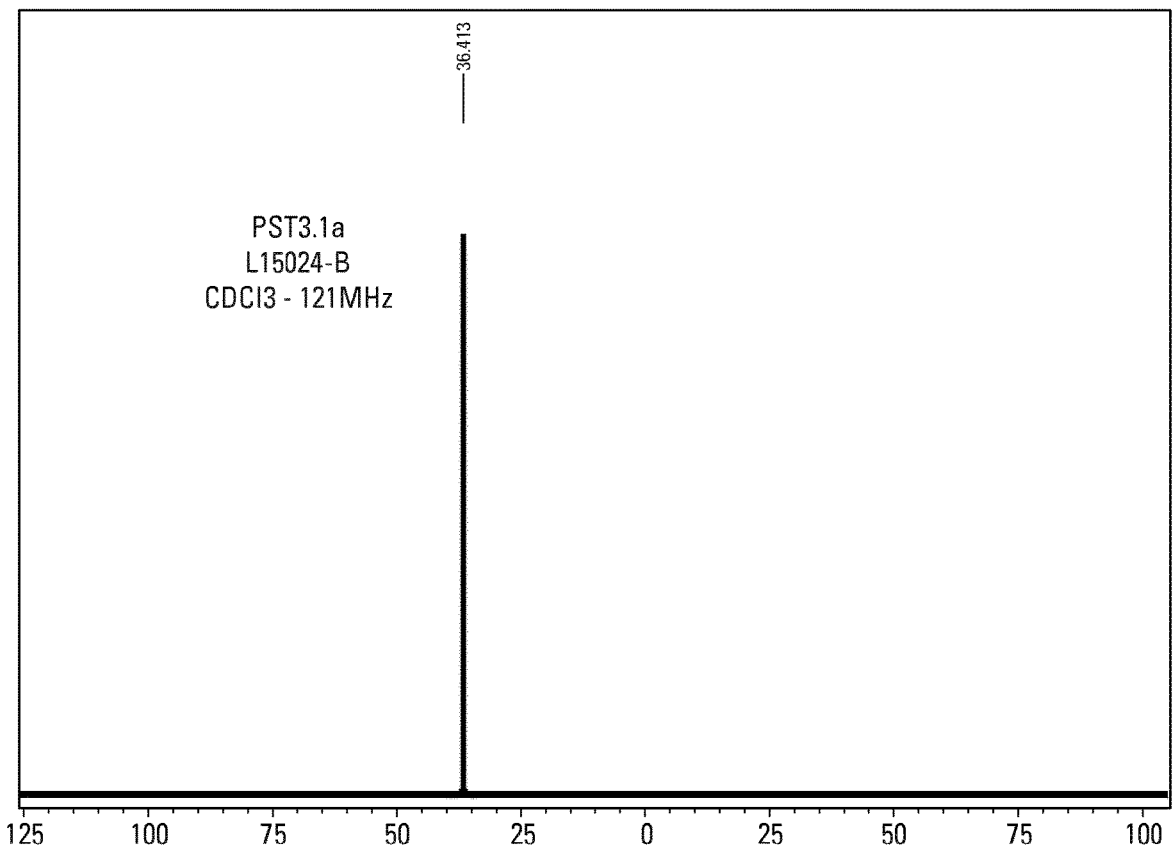
Figure 8:
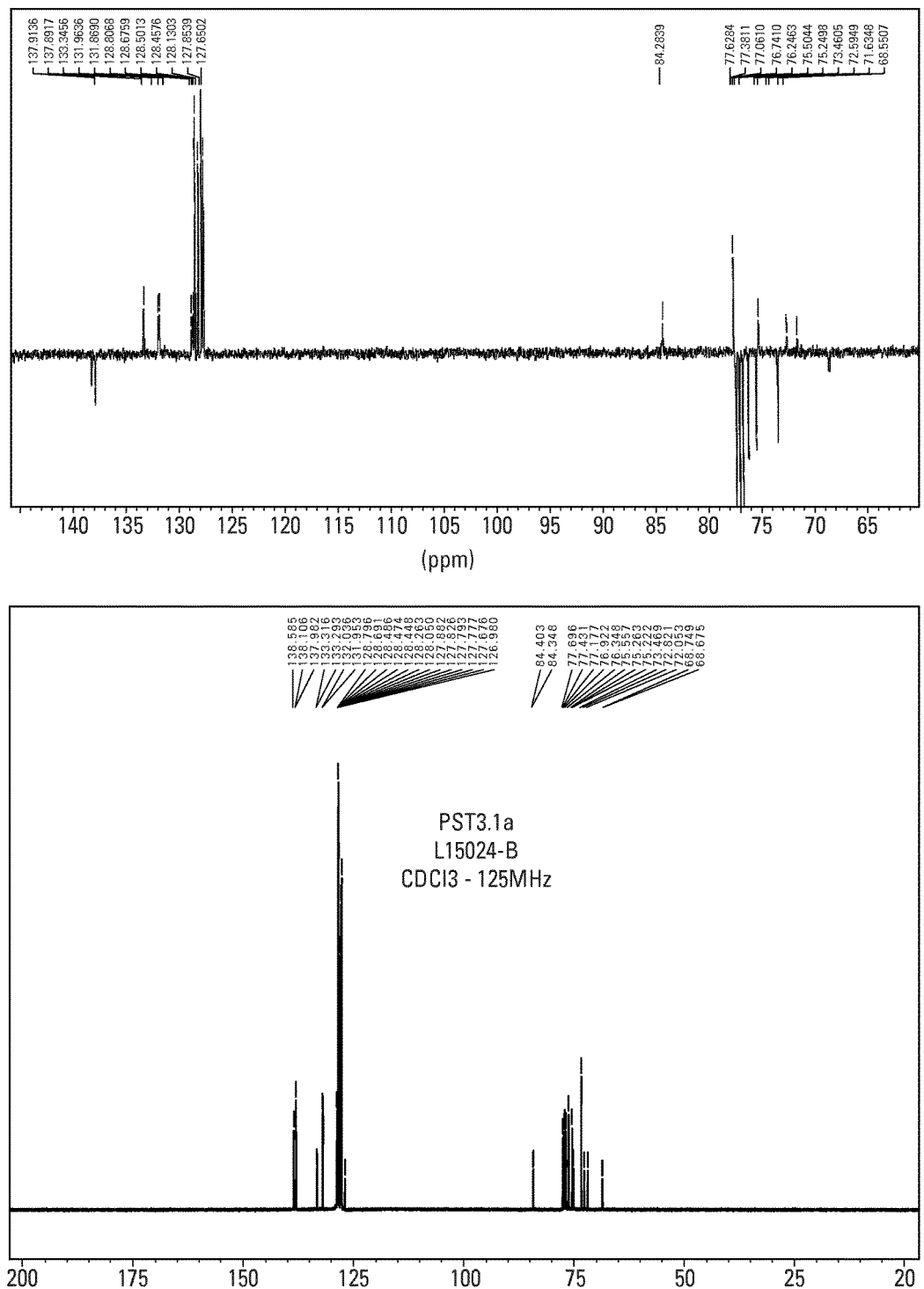
FIG. 8 is the RMN $^{13}$C-CDCl3 spectrum for the crystalline form of the invention (as prepared by example 1), including enlargement of ranges of interest (above)

PST3.1a was confirmed by $^1$H NMR (CDCl3, 500 MHz), $^{31}$P NMR (CDCl3, 121 MHz), and $^{13}$C NMR (CDCl3, 125 MHz). (see FIGS. 6, 7 and 8, respectively).

HPLC at 214 nm: purity=98.4%

The process was highly reproducible. It is interesting to note that starting from 32, 83, 93 and 263 g of compound 3 gave rise to very closed results in terms of yield and purity.

Example 2

Analysis of the Obtained Product
X-ray Powder Diffraction (XRPD)

The analyses of the samples (product obtained by carrying out the above scheme 5) were performed on a PANalytical X'Pert Pro diffractometer, in transmission mode. The sample (few milligrams) was placed between two polymer foils (Kapton® and/or polypropylene). It is worth noting that Kapton® exhibits a broad peak with a low intensity around 2θ=5.5°. The analyses were performed between 2° and 50° (unless stated otherwise). The calibration of the diffractometer was validated before each analytical campaign in order to meet the requirements of the quality system.

TABLE 3

Technical specification of X-ray powder diffraction analyses

| | Sample mode: Transmission |
|---|---|
| Measurement | Scan axis: Gonio |
| | Scan range (°): 1.9960-50.0003 |
| | Step size (°): 0.0263 |
| | Measurement type: Repeated scan (3/5/20/50 times) |
| | Sample offsets: Omega (°): 0.000 |
| | Sample movement: Movement type: Spinning Rotation time (s): 2.0 |
| Used wavelength | Intended wavelength type: Kα1 |
| | Kα1 (Å): 1.540598 |

TABLE 3-continued

Technical specification of X-ray powder diffraction analyses

| | |
|---|---|
| | Kα2 (Å): 1.544426 |
| | Kα2/Kα1 intensity ratio: 0.50 |
| | Kα (Å): 1.541874 |
| | Kβ (Å): 1.392250 |
| | Incident Beam Path: Radius (mm): 240.0 |
| X-ray tube | Name: PW3373/10 Cu LFF DK174558 |
| | Anode Material: Cu |
| | Voltage (kV): 40 |
| | Current (mA): 40 |
| | Focus type: Line (Length (mm): 12.0 width (mm): 0.4 Take-off angle (°): 4.4) |
| X-ray mirror | Name: Inc. Beam Cu W/Si (parabolic MPD) Crystal (W/Si Graded Parabolic) |
| | Acceptance angle (°): 0.8 |
| | Length (mm): 55.3 |
| Slits | Soller slit: Soller 0.04 rad. Opening (rad.): 0.04 |
| | Anti-scatter slit: AS Slit 1.4 mm (mirror) Type: Fixed Height (mm): 1.40 |
| | Divergence slit: Slit Fixed ⅛° |
| | Distance to sample (mm): 140 |
| | Type: Fixed Height (mm): 0.19 Angle (°): 0.1089 |
| | Diffracted Beam Path: Radius (mm): 240.0 |
| Soller slit Detector | Large Soller 0.04 rad. Opening (rad.): 0.04 |
| | Name: PIXcel Type: RTMS detector |
| | PHD - Lower level (%): 25.5 |
| | PHD - Upper level (%): 70.0 Mode: Scanning Active length (°): 3.347 |
| | Instrument/Software |
| | Instrument ID: 0000000011026833 |
| | Application SW: X'Pert Data Collector vs. 2.2j |
| | Instrument control SW: XPERT-PRO vs. 2.1D |

Differential Scanning Calorimetry (DSC)

The analyses were performed on a Perkin Elmer Diamond DSC. The samples (few milligrams of product obtained by carrying out the above scheme 5) were placed in a 25 μL aluminum sample pan and crimped with a punctured cover. Analyses were performed under nitrogen purge (20 mL/min) with temperature scans between 20° C. and 300° C. at 10°/min (unless stated otherwise).

The calibration was validated before each analytical campaign in order to meet the requirements of our quality system.

Thermogravimetry (TGA)

The analyses were performed on a Perkin Elmer Pyris 1 TGA. The samples (few milligrams of product obtained by carrying out the above scheme 5) were placed in an aluminum pan and the cover was crimped. Analyses were performed under nitrogen purge (20 mL/min) and the cover was punctured at the beginning of the analysis.

Temperature scans were carried out between 25° C. and 300° C. at a speed of 10°/min (unless stated otherwise).

The calibration was validated before each analytical campaign in order to meet the requirements of our quality system.

Dynamic Vapor Sorption (DVS)

The analyses were performed on a Surface Measurements System DVS Intrinsic. The samples (few milligrams of product obtained by carrying out the above scheme 5) were placed in an open aluminum pan. Analyses were performed at 25° C.

Relative humidity was scanned between 0% RH and 95% RH with 10% RH steps (40-0-95-0-95; unless stated otherwise). The stability criterion was a variation in mass lower than 0.002% on a 5 min. window (with a minimum step time of 10 min and a maximum of 100 min).

The calibration was validated before each analytical campaign in order to meet the requirements of our quality system.

Infrared Spectroscopy (FTIR-ATR)

Infrared spectra were measured on a Nicolet iS5 FT-IR spectrometer equipped with an iS7 ATR module, with the parameters gathered in Table 4.

TABLE 4

Characteristics for the IR analyses.

| Mode | ATR Diamond |
|---|---|
| Resolution | 4 cm$^{-1}$ |
| Number of scans (measurement): | 32 scans |
| Number of scans (background) | 32 scans |
| Spectrum | 4000 cm$^{-1}$ à 525 cm$^{-1}$, in absorbance |

Results

The obtained powder X-Ray diffraction pattern is presented in FIG. 1.

The crystalline form of compound I is thus characterized by powder x-ray diffraction reflections at about 8.65, 16.06, 16.53, 19.16 and 21.05±0.20, preferably ±0.1, degrees two-theta. This crystalline form can be further characterized by powder x-ray diffraction reflections at about 14.04, 17.69, 19.66, 22.02 and 25.12±0.20 degrees two-theta, or substantially as depicted in FIG. 1 or Table 1 (above).

Figure 2:
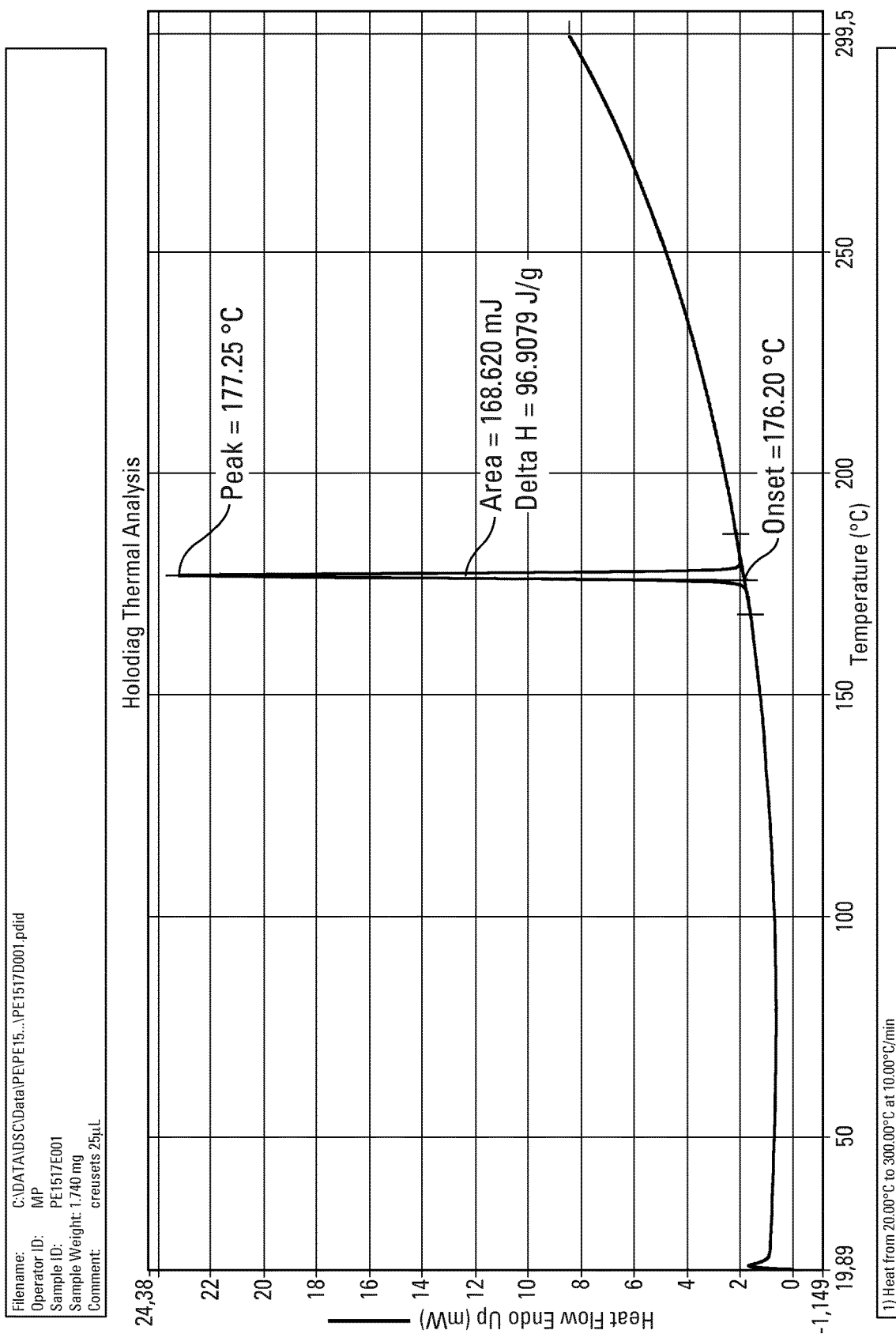
FIG. 2 illustrates a DSC analysis for the crystalline form of the invention (as prepared by example 1).

The DSC thermogram showed an endothermic with an onset at 176.2° C., which corresponds to the melting of the sample. The DSC analysis is presented in FIG. 2.

Figure 3:
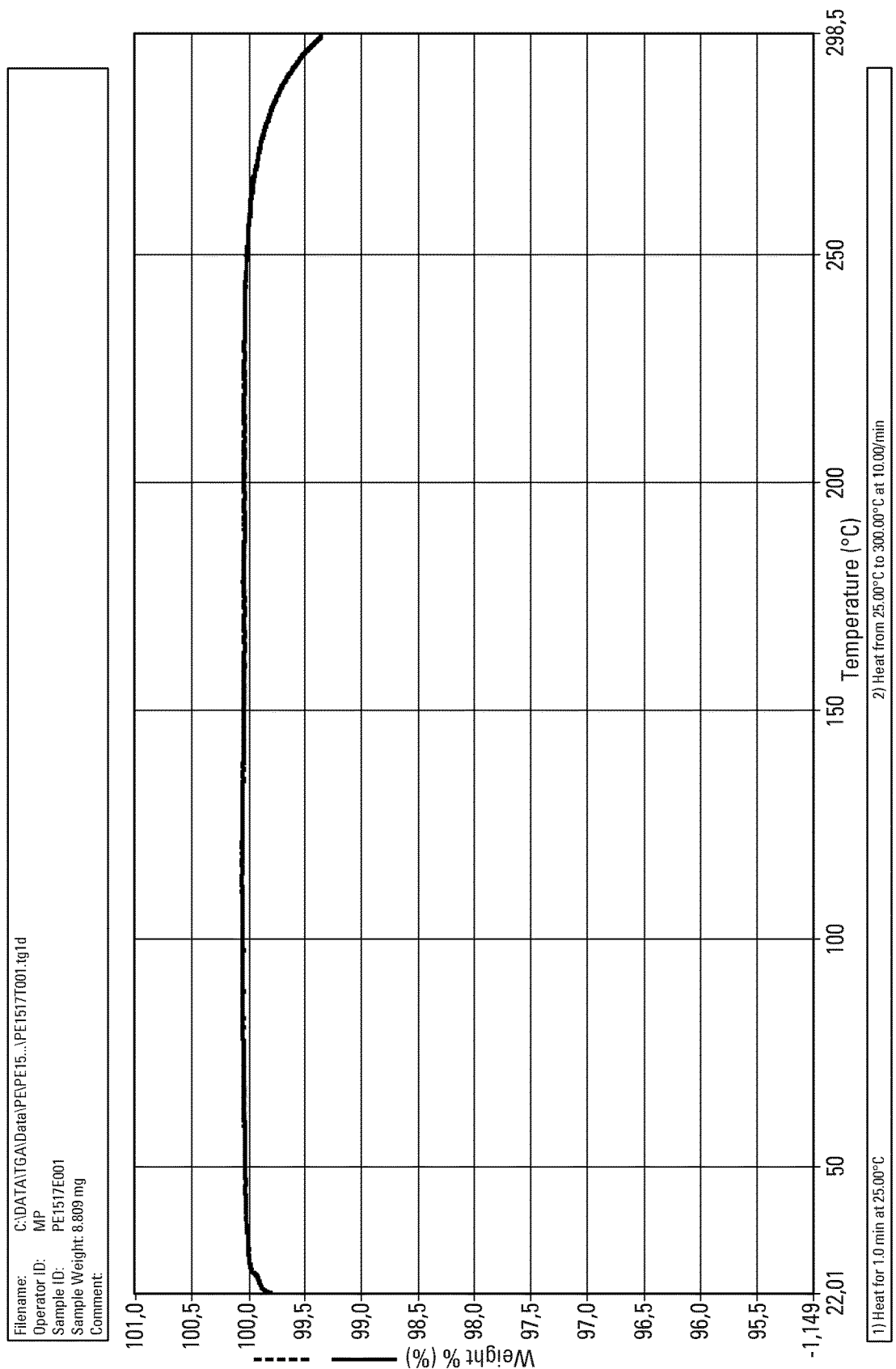
FIG. 3 illustrates a thermogravimetric analysis for the crystalline form of the invention (as prepared by example 1).

The thermogravimetric analysis exhibits no significant weight loss before and after the melting of the sample, up to 250° C. (see FIG. 3). The start of a weight loss above 250° C. may correspond to degradation of the sample.

Figure 4:
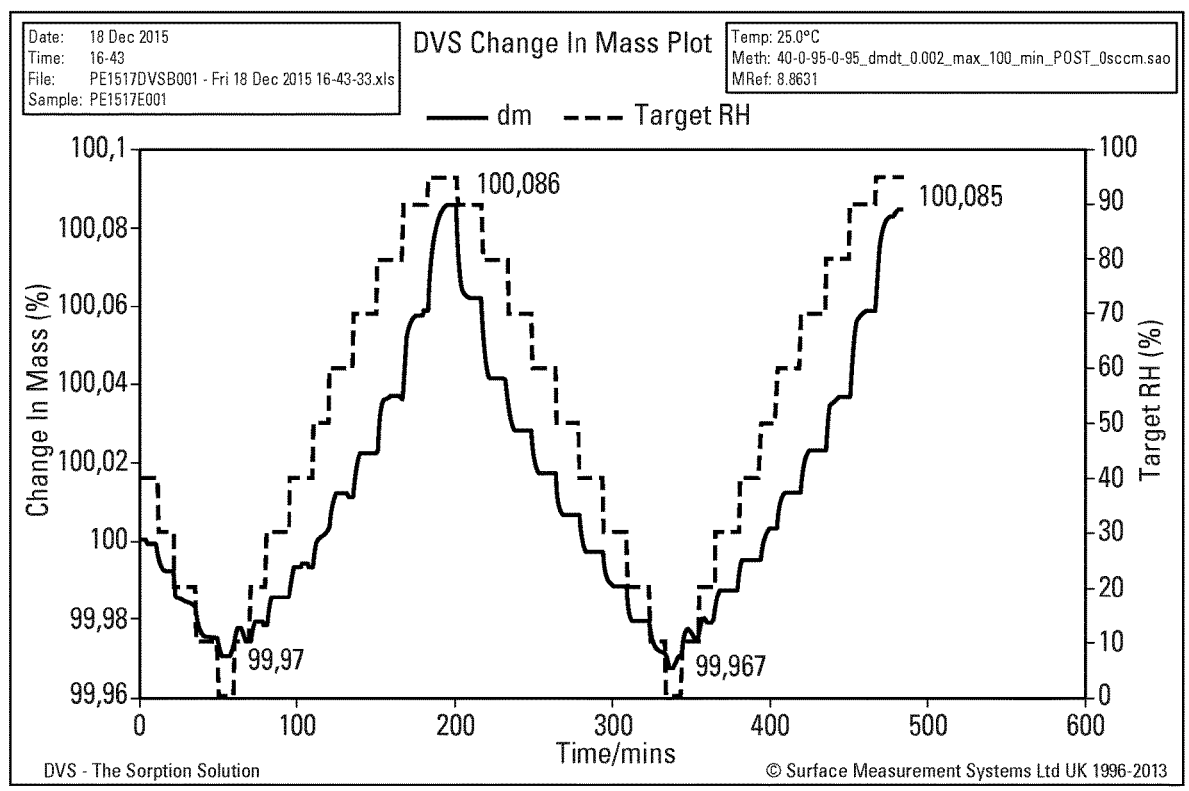
FIG. 4 illustrates the mass change vs. time during RH % steps of the crystalline form of the invention (as prepared by example 1) during the DVS analysis.

The DVS analysis exhibits a loss lower than 0.1% on the drying steps (see FIG. 4). The sample also exhibits a limited gain of 0.1% with respect to the initial weight on the steps at higher relative humidity conditions. Both cycles show similar results. The sample is therefore non-hygroscopic.

Figure 5:
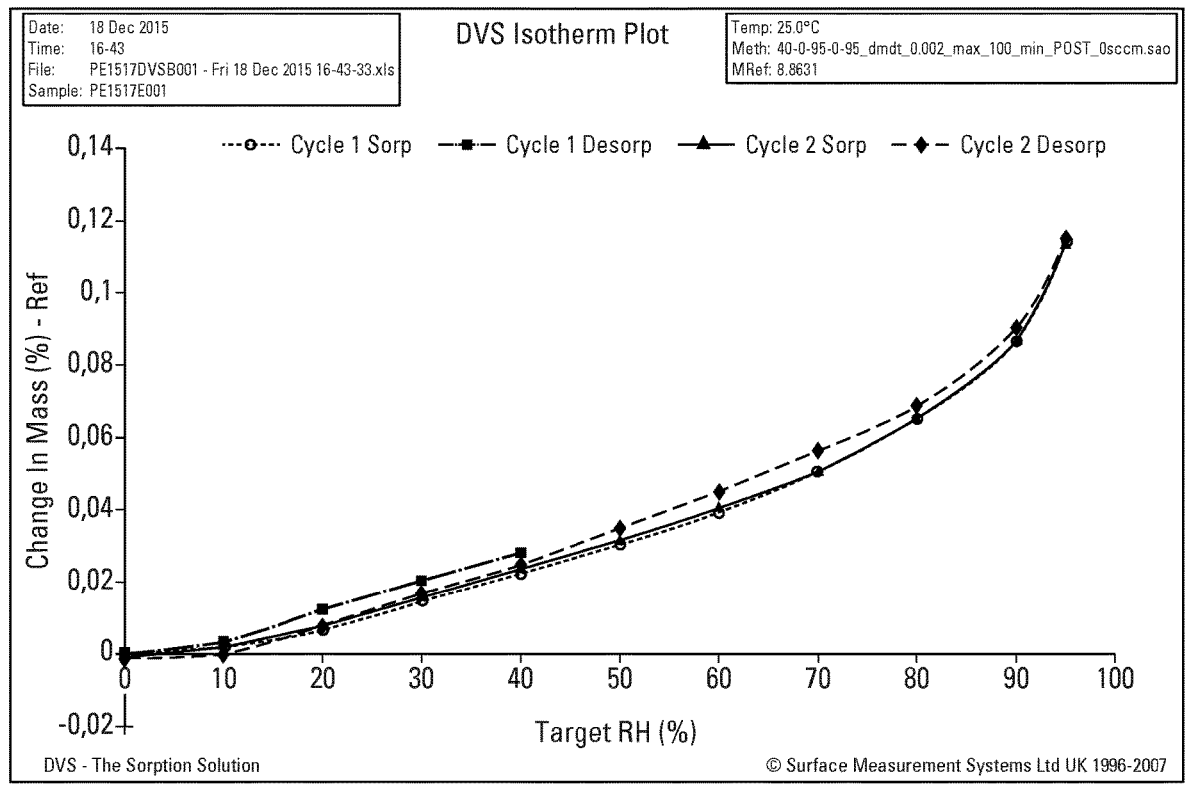
FIG. 5 illustrates the mass values vs. RH % for the crystalline form of the invention (as prepared by example 1) during the DVS analysis.

A plot of the weight variation with respect to the dried sample is also shown on FIG. 5.

On the final step of the analysis, the sample is kept at 95% RH before it is analyzed by X-ray powder diffraction. The XRPD pattern obtained exhibits the same profile as before the DVS analysis.

Example 3

Additional Analysis of the Obtained Product

Compression Test The sample was introduced into a die with 13 mm diameter (m=103.83 mg). The sample was then compressed with a hydraulic press at a pressure of 10 tons for 5 minutes, and immediately analyzed by X-ray diffraction.

Results

The superimposition of the diffraction patterns obtained after the analysis of the whole pellet submitted to a pressure of 10 tons for 5 min with those of the starting material has the same peaks. This result shows the stability of the compound of the invention in solid state after compression. The diffraction pattern obtained is characteristic of the crystalline sample.

Other Polymorphic Forms

Other polymorphic forms could be obtained by recrystallizing out from specific organic solvents starting from the crystalline form of the invention. However, said other polymorphic forms are not stable after several days of maturation at room temperature (more specifically at 25° C.). The same applies by cross-seeding tests where the crystalline form of the invention appears to be the most stable form at 25° C.

The invention claimed is:

1. A crystalline form of 3-Hydroxy-4,5-bis-benzyloxy-6-benzyloxymethyl-2-phenyl-2-oxo-2λ5-[1,2]oxaphosphinane, characterized by powder x-ray diffraction reflections at about 8.65, 16.06, 16.53, 19.16 and 21.05±0.2 degrees two-theta.

2. The crystalline form according to claim 1, wherein it is further characterized by powder x-ray diffraction reflections at about 14.04, 17.69, 19.66, 22.02 and 25.12±0.2 degrees two-theta.

3. The crystalline form according to claim 1, wherein it is further characterized by powder x-ray diffraction pattern as depicted in FIG. 1.

4. The crystalline form according to claim 1, wherein it has a melting point, by Differential Scanning Calorimetry (DSC), of 175.5-177.5° C., at a heating rate of 10° C./min.

5. A method for preparing a crystalline form of 3-Hydroxy-4,5-bis-benzyloxy-6-benzyloxymethyl-2-phenyl-2-oxo-2λ5-[1,2]oxaphosphinane, wherein the method comprises at least one crystallizing step of a solution comprising acetone and a compound of the following formula (I):

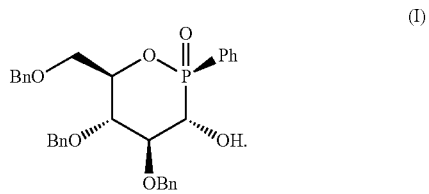 [SMILES: O=[P@@]1(c2ccccc2)O[C@H](COCc2ccccc2)[C@@H](OCc2ccccc2)[C@H](OCc2ccccc2)[C@H]1O]

6. The method according to claim 5, wherein it comprises one, two, three, four, or five crystallizing steps.

7. The method according to claim 5, wherein the crystallizing step of the solution comprising the compound of formula (I) and acetone is the last crystallization step.

8. The method according to claim 7, wherein the crystallizing step(s) preceding the last crystallization step is or are carried out with a solution comprising the compound of formula (I) and a solvent selected in the group consisting of acetone and ethanol, optionally in combination with water or methyl tert-butylether.

9. The method according to claim 7, wherein the crystallizing step(s) preceding the last crystallization step is or are carried out with a solution comprising the compound of formula (I) and ethanol.

10. The method according to claim 5, wherein the method comprises two crystallizing steps with solutions comprising the compound of formula (I) and ethanol are carried out, followed by one crystallizing step of the solution comprising the compound of formula (I) and acetone.

11. The method according to claim 5, wherein, prior to the crystallizing step(s) of claim 5, the compound of formula (I) is prepared by the method comprising the following steps:

a. contacting 2,3,5-tri-O-benzylarabinose 3 and ethyl phenylphosphinate 4 in an organic solvent in the presence of potassium tert-butoxide;

b. adding to the solution of step a) a neutralizing agent of potassium tert-butoxide;
c. adding a water-immiscible organic solvent to the mixture of step b) to allow decantation of the organic layer;
d. washing with water, followed by adding an ether-type or toluene solvent; and
e. recovery of the compound of formula (I).

12. The process according to claim 11, wherein one molar equivalent is used for each compound 3 and 4 at step (a).

13. The process according to claim 11, wherein the organic solvent of step a) is selected in the group consisting of THF, methyl tert-butylether, ethyl acetate, MeTHF, acetone, toluene and a mixture thereof.

14. A pharmaceutical composition comprising the crystalline polymorphic form as defined in claim 1, and one or more pharmaceutically acceptable excipients.

15. A method of palliative therapy of cancer and/or reducing or delaying metastasis, comprising administering to a patient in need thereof an effective amount of the crystalline polymorphic form as defined in claim 1.

16. The crystalline form according to claim 1, wherein it has a melting point, by differential scanning calorimetry (DSC) of 176.2° C.±0.4° C., at a heating rate of 10° C./min.

\* \* \* \* \*